United States Patent
Mafi

(10) Patent No.: US 8,852,253 B2
(45) Date of Patent: Oct. 7, 2014

(54) ANCHORING CANNULA

(75) Inventor: Masourmeh Mafi, Mountain View, CA (US)

(73) Assignee: Kyphon SARL, Neuchatel (CH)

( * ) Notice: Subject to any disclaimer, the term of this patent is extended or adjusted under 35 U.S.C. 154(b) by 169 days.

(21) Appl. No.: 13/360,327

(22) Filed: Jan. 27, 2012

(65) Prior Publication Data

US 2013/0197592 A1     Aug. 1, 2013

(51) Int. Cl.
*A61B 17/04*   (2006.01)
*A61B 17/86*   (2006.01)
*A61F 2/08*    (2006.01)

(52) U.S. Cl.
USPC .......................................... 606/323; 600/206

(58) Field of Classification Search
CPC .......................... A61B 17/3421; A61B 17/3439
USPC ............... 606/323, 92–94; 600/204, 205, 206
See application file for complete search history.

(56) References Cited

U.S. PATENT DOCUMENTS

| | | |
|---|---|---|
| 5,295,994 A | 3/1994 | Bonutti |
| 5,320,611 A | 6/1994 | Bonutti et al. |
| 5,514,153 A | 5/1996 | Bonutti |
| 5,674,240 A | 10/1997 | Bonutti et al. |
| 5,961,499 A | 10/1999 | Bonutti et al. |
| 6,171,299 B1 | 1/2001 | Bonutti |
| 6,190,357 B1 | 2/2001 | Ferrari et al. |
| 6,312,443 B1 | 11/2001 | Stone |
| 6,338,730 B1 | 1/2002 | Bonutti et al. |
| 6,358,266 B1 | 3/2002 | Bonutti |
| 6,613,038 B2 | 9/2003 | Bonutti et al. |
| 6,730,095 B2 * | 5/2004 | Olson et al. ..................... 606/93 |
| 6,814,715 B2 | 11/2004 | Bonutti et al. |
| 7,311,719 B2 | 12/2007 | Bonutti |
| 8,568,308 B2 * | 10/2013 | Reznik .......................... 600/227 |

* cited by examiner

*Primary Examiner* — Andrew Yang
(74) *Attorney, Agent, or Firm* — Sorell Lenna & Schmidt LLP

(57) ABSTRACT

An apparatus and method for an anchoring cannula including a first cannula having a proximal end, a distal end, a longitudinal axis and a lumen extending from the proximal end to the oppositely disposed distal end along the longitudinal axis. A second cannula is concentrically arranged within the lumen of the first cannula, the second cannula having a proximal end, a distal end and a lumen extending from the proximal end to the oppositely disposed distal end along the longitudinal axis. The second cannula includes an expandable portion connected to the distal end that is configured to expand when the second cannula is advanced out of the distal end of the first cannula and to change to an unexpanded configuration when retracted back into the distal end of the first cannula.

20 Claims, 5 Drawing Sheets

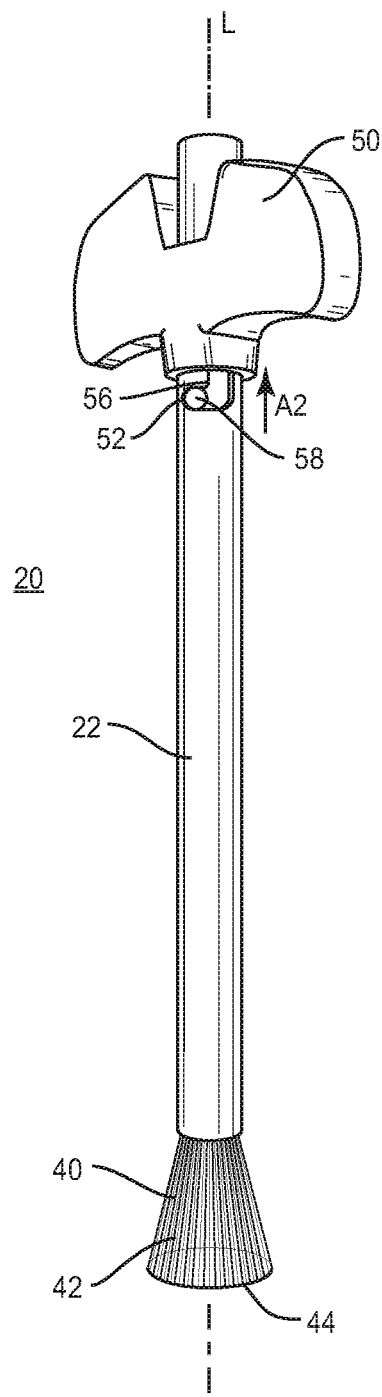
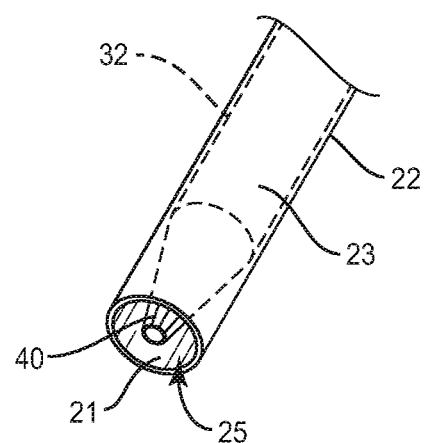
FIG. 5
FIG. 6

ANCHORING CANNULA

TECHNICAL FIELD

The present disclosure provides cannulas for use in surgical procedures and, more particularly, to an anchoring cannula possessing a material on or as part of a portion thereof which alters its configuration upon the deployment to anchor the cannula to tissue upon insertion in a patient's body. Methods of using such a cannula are also provided.

BACKGROUND

During minimally invasive surgical procedures, cannulas are utilized to provide an access port for surgical instruments and for treating conditions such as fractures. A sharp trocar may be positioned within the cannula and utilized to puncture or pierce the tissue to access the damaged bone. Thereafter the trocar may be removed, leaving the cannula in place providing the access port to the site of treatment. Stabilization of the cannula during treatment is very important, as the ports can be accidentally ejected from the patient or moved while materials, such as bone cement, are being delivered resulting in less perfect treatment and increased procedure time.

In the bone where there is minimal cancelous bone, such as a distal radius, when the cannula is inserted, it cannot be easily stabilized and does not remain stationary. This unstabilization can cause imprecise disbursement of material, such as bone cement. To increase stabilization, use of an anchoring cannula at the surgical site adjacent to a fracture or a break in a portion of a bone is needed.

SUMMARY OF THE INVENTION

This application relates to an apparatus and method for an anchoring cannula having a first cannula including a proximal end, a distal end, a longitudinal axis and a lumen extending from the proximal end to the oppositely disposed distal end along the longitudinal axis. A second cannula is concentrically arranged within the lumen of the first cannula. The second cannula having a proximal end, a distal end and a lumen extending from the proximal end to the oppositely disposed distal end along the longitudinal axis. The second cannula includes an expandable portion connected to the distal end that is configured to expand when the second cannula is advanced out of the distal end of the first cannula and to return to an unexpanded configuration when retracted back into the distal end of the first cannula.

In one embodiment, an anchoring cannula includes an outer cannula having a proximal end, a distal end, a longitudinal axis and a lumen extending from the proximal end to the oppositely disposed distal end of the outer cannula along the longitudinal axis. Each of the proximal and distal ends includes an opening therein. An inner cannula configured to fit within the lumen of the outer cannula is provided. The inner cannula having a proximal end, a distal end, a longitudinal axis and a lumen extending from the proximal end to the oppositely disposed distal end along the longitudinal axis. The distal end includes an expandable portion connected to the distal end that is configured to expand when the inner cannula is advanced out of the distal end of the outer cannula and to collapse when retracted back into the outer cannula. The expandable portion is constructed of polymer and shape-set material that expands when the inner cannula is advanced out of the distal end of the outer cannula and collapses when the retracted back into the outer cannula. An actuator member is in contact with the inner cannula wherein moving the actuator back and forth from a first position to a second position extends and retracts the expandable portion of the inner cannula from the distal end of the outer cannula. The anchoring cannula further includes a locking mechanism configured to lock the inner cannula to the outer cannula.

A method for treating a fracture including inserting the anchoring cannula of the present disclosure into bone adjacent to a fracture is also provided. The method includes advancing the second cannula out of the distal end of the first cannula to expand the expandable portion so that the at least a part of the expandable portion is in contact with bone so as to stabilize the anchoring cannula in place. Treating the fracture adjacent to the anchoring cannula. Retracting the second cannula back into the distal end of the outer cannula so as to collapse the expandable portion of the second cannula and removing the anchoring cannula from bone.

BRIEF DESCRIPTION OF THE DRAWINGS

The present disclosure will become more readily apparent from the specific description accompanied by the following drawings, in which:

FIG. 5 is a perspective view of the anchoring cannula of FIG. 4 with the expandable portion fully expanded;

FIG. 6 is a perspective view of the distal end of the anchoring cannula of FIG. 1;

DETAILED DESCRIPTION

Figure 1:
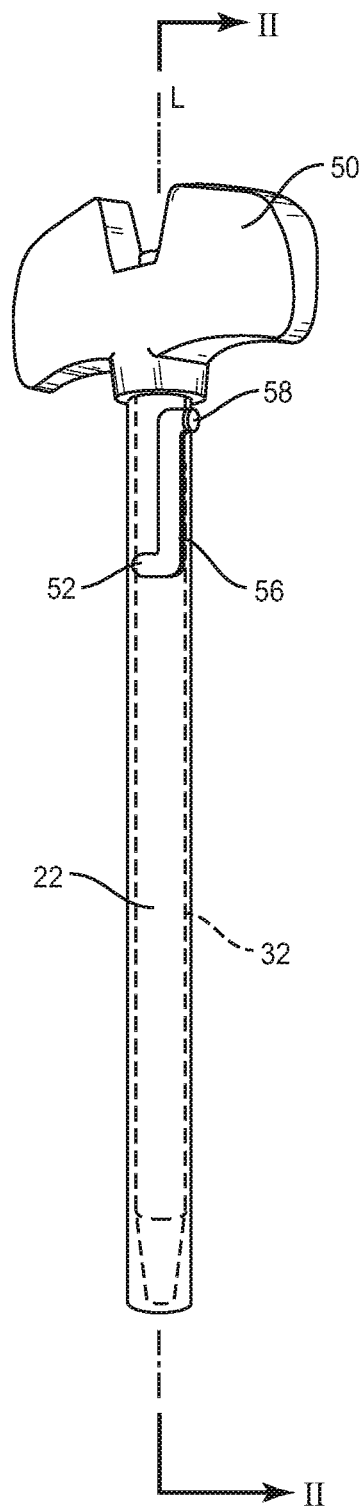
FIG. 1 is a perspective view of the anchoring cannula in accordance with the principles of the present disclosure.

An apparatus and method is described for an anchoring cannula. For illustrative purposes, the apparatus and method shall be described in the context of injecting a bone void filler/bone cement into a portion of a long bone or vertebra of a patient to treat bone fractures, although the apparatus and methods can be used to treat other conditions.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, distal and proximal, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament and/or bone, repairing a fracture or break in bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
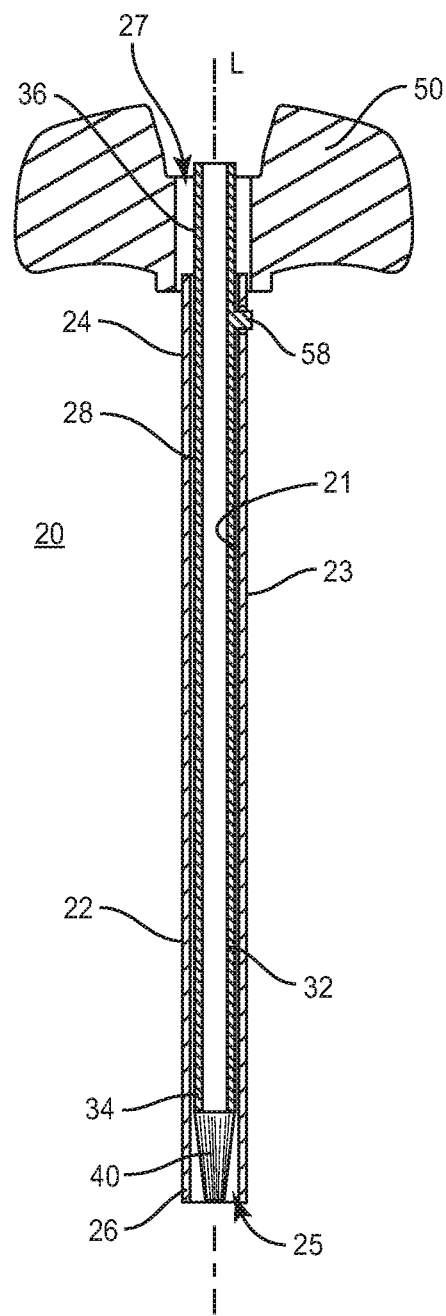
FIG. 2 is a cross sectional view of one particular embodiment of the anchoring cannula of FIG. 1 along the lines II-II.
Figure 3:
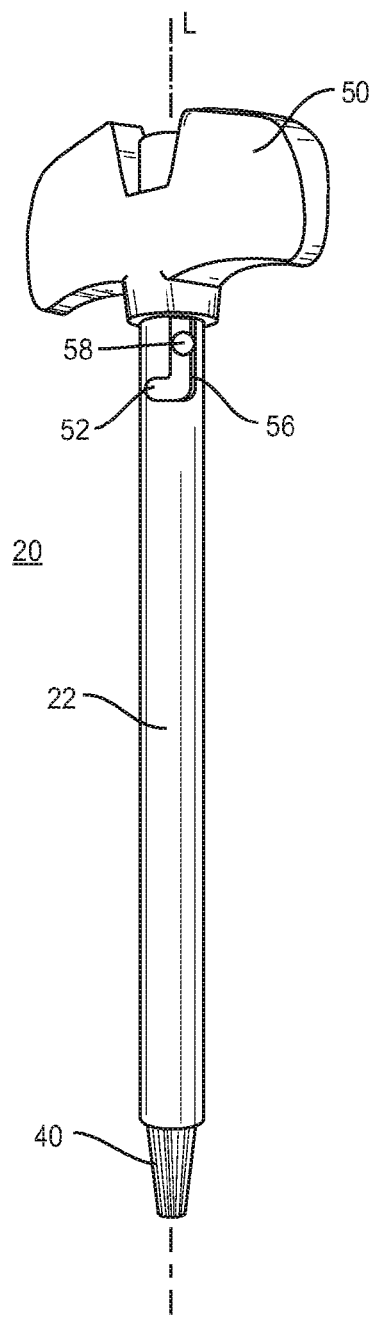
FIG. 3 is a perspective view of the anchoring cannula of FIG. 1 with the expandable portion disposed outside of the inner cannula but not expanded.
Figure 4:
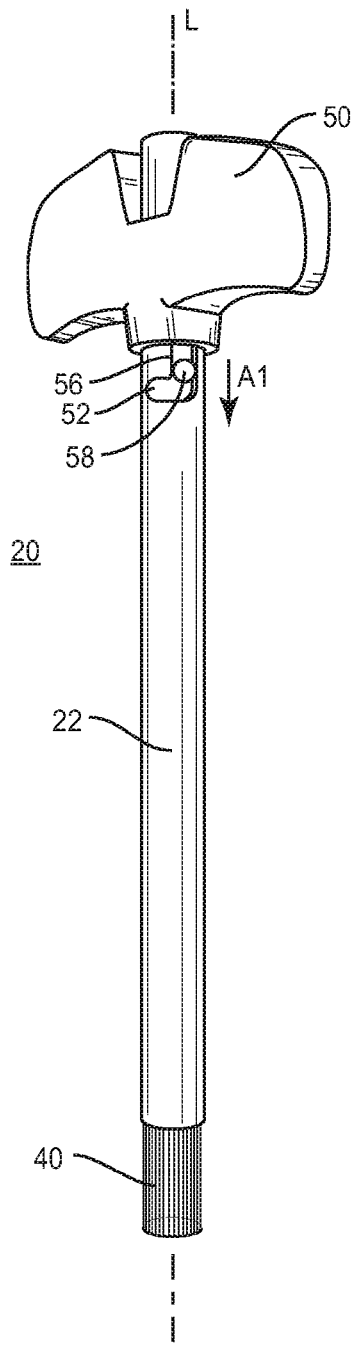
FIG. 4 is a perspective view of the anchoring cannula of FIG. 3 with the expandable portion beginning to expand to its expanded configuration.
Figure 7:
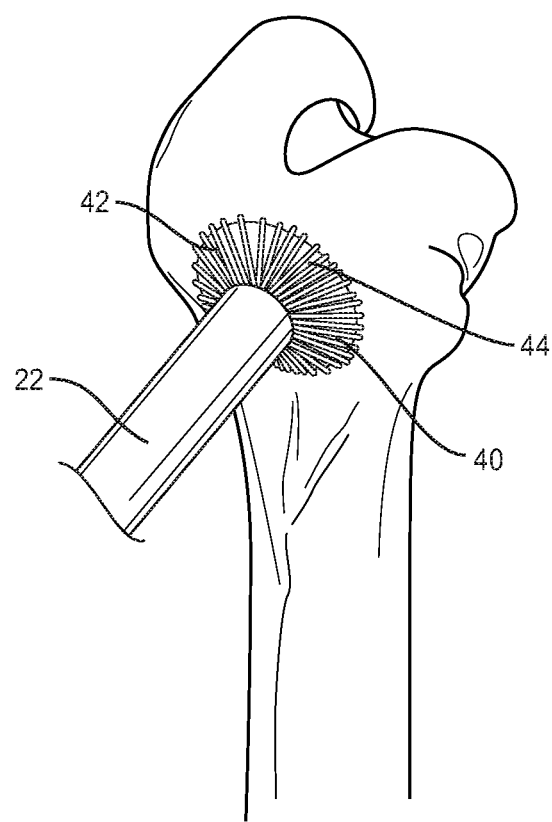
FIG. 7 is a perspective view of the anchoring cannula of FIG. 1 disposed in a surgical site; and Like reference numerals indicate similar parts throughout the figures.

The following discussion includes a description of an anchoring cannula for treating fractures, including using an inflatable bone tamp, drills and for delivering bone void filler, such as, for example, auto graft, allograft, demineralized bone material, mineral composites, blocks, granules and pellets and bone cement, such as, for example, PMMA-based material (HVR, Activos, Activos 10, Spine-05), Calcium Phosphate (Skaffold, Norian, Hydroset, Kyphos FS) and Calsium Sufacte (Wright Medical), as well as other injectables. It also includes a description of related methods of employing the anchoring cannula in accordance with the principles of the present disclosure. Alternate embodiments are also disclosed. Reference will now be made in detail to the exemplary embodiments of the present disclosure, which are illustrated in the accompanying figures. Turning now to FIGS. 1-7, there is illustrated components of an anchoring cannula 20 in accordance with the principles of the present disclosure.

The components of the anchoring cannula 20 can be fabricated from biologically acceptable materials suitable for medical apparatuses, including metals, synthetic polymers, ceramics, thermoplastic and polymeric material and/or their composites. For example, the components of the anchoring cannula 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan, Fe—Mn—Si and Fe—Ni—Co—Ti composites), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers based materials, polymeric rubbers, polyolefin rubbers, semi-rigid and rigid materials, thermoplastic elastomers, thermoset elastomers, elastomeric composites, rigid polymers including polyphenylene, polyamide, polyimide, polyetherimide, polyethylene, epoxy, polyacrylate and composites of metals and calcium-based ceramics, composites of PEEK and calcium based ceramics, and combinations of the above materials. Various components of the anchoring cannula may have material composites, including the above materials, to achieve various desired characteristics such as strength, rigidity, elasticity, compliance, and biomechanical performance, durability and to provide a non-stick surface. The components of the anchoring cannula system 20 may be monolithically formed, integrally connected or include fastening elements and/or coupling components, as described herein.

As will be described fully herein, one embodiment of the present disclosure incorporates and utilizes one or more material(s), which exhibit what is known as "superelasticity". The term "superelasticity", as used herein, shall generally mean the ability of a material to undergo large elastic deformations without the onset of plasticity or permanent deformation.

One particular group of metallic alloys, known as "shape memory alloys" is known to exhibit superelastic properties. Such shape memory alloys also demonstrate a "shape memory" phenomenon whereby the alloy is generally transformable, back and forth, between a low temperature configuration and a high temperature configuration. Transformation from the low temperature configuration to the high temperature configuration generally occurs as the alloy passes from its martensitic state to its austenitic state. Subsequent transformation from the high temperature configuration back to the low temperature configuration occurs as the alloy passes from its austenitic state to its martensitic state.

These unique alloys also show a superelastic behavior if deformed at a temperature which is slightly above their transformation temperatures. This effect is caused by the stress-induced formation of some martensite above its normal temperature. Because it has been formed above its normal temperature, the martensite reverts immediately to undeformed austenite as soon as the stress is removed. This process provides a very springy, "rubberlike" elasticity in these alloys.

In one embodiment, as shown in FIGS. 1-7 anchoring cannula 20 includes a first cannula, such as, for example an outer cannula 22 and a second cannula, such as, for example, an inner cannula 32. Outer cannula 22 extends between a proximal end 24 and a distal end 26 along a longitudinal axis L. In an alternate embodiment, a portion of the inner and outer cannula, 22, 32, can have alternate orientations relative to longitudinal axis L, such as, for example, parallel, transverse and/or other angular orientations such as acute or obtuse, co-axial and/or may be offset or staggered. Outer cannula 22 includes an inner surface 21 and an outer surface 23. Inner surface 21 defines a lumen 28 that extends along longitudinal axis L between proximal end 24 and distal end 26.

It is contemplated that outer cannula 22 be variously configured, such as, for example, round, oval, oblong, square, rectangular, polygonal, irregular, uniform, non-uniform, offset, staggered, tapered, consistent or variable, depending on the requirements of a particular application. Outer surface 23 may be rough, arcuate, undulating, mesh, porous, semi-porous, dimpled and/or textured according to the requirements of a particular application.

Proximal end 24 and distal end 26 each include an opening 25 and 27. Openings 25 and 27 can be variously configured, such as, for example, round, oval, oblong, square, rectangular, polygonal, irregular, uniform, non-uniform, offset, staggered, tapered, consistent or variable, depending on the requirements of a particular application. Openings 25 and 27 do not need to have the same shape but are configured to provide access to and out of lumens 28, 38 of inner and outer cannulae 22, 32. In one embodiment, in accordance with the disclosure, it is contemplated that outer cannula 22 includes a cutting edge at distal end 26 configured to cut into the tissue wherein anchoring cannula 20 is to be used. In the alternative, distal end 26 can include a threaded portion, fluted tip as well as other surgical configurations. In the alternative, a separate device can be used to cut a primary access port for anchoring cannula 20 and the cutting edge shaves away at the edges of the primary access point to gain entry into the surgical site.

Inner cannula 32 extends along longitudinal axis L between a proximal end 34 and a distal end 36 and inner cannula 32 is configured to fit within lumen 28, such as, for example, inner cannula 32 is concentrically arranged within lumen 28 at least in part. It is contemplated that inner cannula 32 can be variously configured, such as, for example, round, oval, oblong, square, rectangular, polygonal, irregular, uniform, non-uniform, offset, staggered, tapered, consistent or variable, depending on the requirements of a particular application as long as it fits within outer cannula 22. The surface of inner cannula 32 can be coated with a lubricant to allow it to slide within lumen 28 of outer cannula 22. Distal end 36 includes an expandable portion 40 connected thereto that is further discussed below. The expandable portion 40 can be a separate member that is connected to the distal end 36 of inner cannula 32 for example, it can be glued, heat-sealed or mechanically fastened. In the alternative, inner cannula 32 and expandable portion 40 can be, at least in part, monolithically formed.

In one embodiment in accordance with the present disclosure, inner cannula 32 includes an actuator mechanism 50 disposed at proximal end 24 of outer cannula 22. Outer surface 23 of outer cannula 22 includes a cavity, such as for example, an elongated slot 56 disposed at its proximal end 24. Elongated slot 56 allows for movement of actuator mechanism along longitudinal axis L. Actuator mechanism 50 includes a pin 58 that engages elongated slot 56. In one embodiment, pin 58 is connected to inner cannula 32 so that movement of pin 58 by actuator mechanism 50 moves the inner cannula 32 in the direction of movement of actuator mechanism 50. That is, actuator mechanism 50 moves along longitudinal axis L as shown by arrow A1, and slides from a first position thereby moving inner cannula 32 in the same direction. Moving actuator mechanism 50 in the A1 direction advances inner cannula 32 out from distal end 26 allowing expandable portion 40 to be in its expanded configuration. Advancing expandable portion 40 out of distal end 26, distal end 26 is no longer restricted from expanding by the walls of lumen 28 of outer cannula 22 and therefore expands to its expanded configuration. Moving actuator mechanism 50 back from the second position, as shown by arrow A2, slides actuator mechanism 50 back to the first position thereby retracting inner cannula 32 into distal end 26 and returning expandable portion 40 to its unexpanded configuration. Actuator mechanism 50 includes a locking mechanism configured to lock inner cannula 32 in a position certain with respect to outer cannula 22. It is contemplated that locking mechanism is configured as cavity 52 that is disposed transverse to elongated slot 56 such that actuator mechanism 50 can be rotated to move pin 58 into cavity 52 to prevent axial movement along longitudinal axis L.

In one embodiment, expandable portion 40 is entirely within outer cannula 32 when in the collapsed configuration. At least a portion of expandable portion 40 contacts the inner surface 21 of outer cannula 22 so as to maintain it in the collapsed configuration. In an alternative embodiment, collapsed expandable portion 40 is positioned partially within outer cannula 22 so that the walls of outer cannula 22 is in contact with the expandable portion keeping it in an unexpanded configuration. In this embodiment, the expandable portion 40 can be tapered to facilitate entry into the surgical site. Once fully advanced from the outer cannula 22, expandable portion 40 expands to its unexpanded configuration as discussed above.

It is contemplated that expandable portion 40 can be constructed exclusively of shapeset alloy, shape memory polymer with non-shape memory or with a polymeric material. Such shapeset materials possess a permanent shape and a temporary shape. The temporary shape of expandable portion 40 can be tapered so as to make it easier to introduce the cannula into a patient's body. The permanent shape is an expanded configuration, which enhances the retention of the cannula at the site of the procedure.

As stated above, the expandable portion 40 may also have polymeric materials connected to the shapeset material such that polymeric materials have shapeset material connecting them together to form the expandable portion 40. The polymeric materials are rigid and once the shapeset material is allowed to expand the polymeric material provides additional anchoring properties to the expandable portion 40. That is, the polymer segments of the expandable portion are configured to contact the inner bone surfaces, for example cancelous bone, when in the expanded sates so as to anchor the cannula in place. Suitable polymeric materials to be used with the shapeset materials includes, for example, polyurethanes, poly(styrene-butadiene) block copolymers, polynorbornenes, caprolactones, dioxanones, diol esters including oligo(epsilon caprolactone)diol, lactic acid, lactide, glycolic acid, glycolide, ether-ester diols including oligo(p-dioxanone)diol, carbonates including trimethylene carbonate, combinations thereof, and the like. In one embodiment, the shape memory polymer may be a copolymer of two components with different thermal characteristics, such as oligo (epsilon-caprolactone)dimethacrylates and butyl acrylates including poly(epsilon-caprolactone)dimethacrylate-poly(n-butyl acrylate), or a diol ester and an ether-ester diol such as oligo(epsilon caprolactone)diol/oligo(p-dioxanone)diol copolymers. These multi-block oligo(epsilon-caprolactone)diol/oligo(p-dioxanone)diol copolymers possess two block segments: a "hard" segment and a "switching" segment linked together in linear chains.

It is contemplated that expandable portion 40 be self-expanding due to the spring forces inherent in the shapeset materials and design. In one embodiment in accordance to the disclosure the shapeset material used in expandable portion 40 is a Ni—Ti-based alloy such as Nitinol, or iron based alloy such as Fe—Mn—Si or Fe—Ni—Co-T, copper-aluminum-nickel (CU—Al—Ni), copper-zinc-aluminum (Cu—Zn—Al) and Fe—Mn—Si—Cr. With shapeset materials, the shape of expandable portion 40 can be predetermined. Additionally, expandable portion 40 can be retrieved, repositioned, or removed by retracting the distal end back into the outer cannula 22 thereby forcing expandable portion 40 into its unexpanded configuration. Expandable portion 40 can have a material cross section in the shape of a rectangle, circle, triangle, trapezoid, or any other shape providing a desired bone interaction. Expandable portion 40 can be configured to exhibit different expansion properties, such that expansion results in a non-cylindrical profile (e.g., outwardly tapering, inwardly tapering, ovoid, peanut-shaped, etc.). It is contemplated that at least the expandable portion 40 of the inner cannula 32 maintain a snug fit within the outer cannula 22 so as to prevent movement of the inner cannula 32 during delivery into the surgical site.

As stated above, expandable portion 40 can be constructed of polymer and shapeset materials such as, for example, polymer strips 42 interconnected by a shapeset material 44 to form a flower-like structure. That is, having pedals made of polymers connected together by shapeset material. It is contemplated that other material combinations and shapes can be utilized. The shape of expandable portion 40 can be the same or similar to the cross section of outer cannula 22 for ease in maintaining the unexpanded configuration.

In assembly and use, anchoring cannula 20 is employed with a surgical procedure for treatment of a disorder affecting a section of bone, such as a fracture, for example in the distal radius, tibial plateau or proximal humerus of a patient, as discussed herein. In use, to treat the affected section, a medical practitioner obtains access to the bone in any appropriate manner, such as through incision and retraction of tissues. Once the bone is exposed the cannula can be used to create and enter an access port adjacent to a fracture to be treated. It is envisioned that anchoring cannula 20 may be used in any existing surgical method or technique including open surgery, mini-open surgery, minimally invasive surgery and percutaneous surgical implantation, whereby the site is accessed through a micro-incision, or sleeve that provides a protected passageway to the area. Once access to the surgical site is obtained, anchoring cannula 20 can be deployed so to deliver an agent, such as bone void filler/bone cement, to treat the condition, such as repair the fracture.

In one particular embodiment, use of the anchoring cannula 20 is delivered into the surgical site adjacent to a fracture or a break in a portion of a bone such as the distal radius, tibial plateau or proximal humerus as well as other bone sites. These bone sites have minimal cancelous bone and therefore when the cannula is inserted, it cannot be easily stabilized and does not remain stationary. This unstabilization can cause imprecise disbursement of material, such as bone void filler/bone cement. To facilitate stabilization of the cannula, expandable portion 40 is used and when deployed is disposed between an expanded configuration and an unexpanded configuration. When anchoring cannula 20 is inserted into the surgical site, expandable portion 40 is in its unexpanded configuration within the outer cannula 22. Once in position, inner cannula 32 is advanced out of outer cannula 22 by moving actuator mechanism 50 from a first position to a second position so as to advance inner cannula 22 out of distal end 26 of outer cannula 22. As inner cannula 22 exits distal end 26, expandable portion 40 begins to expand. When expandable portion 40 is completely disposed outside of outer cannula 22, expandable portion is in its fully expanded configuration. Expandable portion 40 stabilizes the cannula in place by pressing against the existing cancelous bone thereby allowing for precise delivery of bone void filler/bone cement, or deployment of other agents and/or surgical tools that may be required. For further stability, actuator mechanism 50 can be locked in place to further stabilize the cannula. When inner cannula 32 is retracted back into outer cannula 22, expandable portion 40 collapses to its unexpanded configuration and the cannula system can be removed.

It is contemplated that in addition to bone void filler/bone cement, other agents can be delivered to a surgical site using anchoring cannula 20. These agents include therapeutic polynucleotides or polypeptides. It is further contemplated that these agents may also include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of anchoring cannula 20 can be made to include radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration. It is contemplated that the first or second cannula can include markers so as to determine the placement of the cannula in the surgical site.

It is envisioned that the use of microsurgical and image guided technologies may be employed to access, view and repair bone deterioration or damage, in conjunction with the anchoring cannula 20.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An anchoring cannula comprising:
a first cannula having a proximal end, a distal end, a longitudinal axis and a lumen extending from the proximal end to the oppositely disposed distal end along the longitudinal axis, the first cannula including a slot defining an upper limit and a lower limit, and
a second cannula concentrically arranged within the lumen of the first cannula, the second cannula having a proximal end, a distal end, a lumen extending from the proximal end to the oppositely disposed distal end along the longitudinal axis and an actuator member including a in configured for engagement with the slot, the second cannula including an expandable portion connected to the distal end that is configured to expand when the second cannula is advanced out of the distal end of the first cannula and to return to an unexpanded configuration when retracted back into the distal end of the first cannula.

2. An anchoring cannula of claim 1, wherein the expandable portion of the second cannula is constructed, at least in part, of a shapeset material.

3. An anchoring cannula of claim 1, wherein the expandable portion of the second cannula is constructed of polymer and shapeset material and is configured to expand when the second cannula is advanced out of the distal end of the first cannula and to change to an unexpanded configuration when retracted back into the distal end of the first cannula.

4. An anchoring cannula of claim 1, wherein the expandable portion comprises polymer strips interconnected by a shapeset material to form a tapered configuration when unexpanded and to expand radially when advanced from the first cannula.

5. An anchoring cannula of claim 1, wherein moving the pin from a first position to a second position advances the second cannula from the distal end of the first cannula and moving the actuator from the second position back to the first second position retracts the second cannula back into the distal end of the first cannula.

6. An anchoring cannula of claim 5, wherein the actuator member further comprises a locking mechanism configured to lock the second cannula in a position with respect to the first cannula.

7. An anchoring cannula of claim 1, wherein the distal end of the first cannula has a cutting edge.

8. An anchoring cannula of claim 3 wherein the polymer is selected from the group consisting of polyaryletherketone (PAEK) including polyetheretherketone (PEEK), polyetherketoneketone (PEKK) and polyetherketone (PEK), carbon-PEEK composites, PEEK-BaSO.sub.4 polymeric rubbers, polyethylene terephthalate (PET), fabric, silicone, polyurethane, silicone-polyurethane copolymers based materials, polymeric rubbers, polyolefin rubbers, semi-rigid and rigid materials, thermoplastic elastomers, thermoset elastomers, elastomeric composites, rigid polymers including polyphenylene, polyamide, polyimide, polyetherimide, polyethylene, epoxy, and composites of metals and calcium-based ceramics, composites of PEEK and calcium based ceramics, and combinations thereof.

9. An anchoring cannula of claim 8 wherein the shapeset material is a Ni—Ti-based alloy such as Nitinol, an iron based alloy such as Fe—Mn—Si or Fe—Ni—Co-T Cu—Al—Ni, Cu—Zn—Al and Fe—Mn—Si—Cr.

10. An anchoring cannula comprising:
an outer cannula having a proximal end, a distal end, a longitudinal axis and a lumen extending from the proximal end to the oppositely disposed distal end of the outer cannula along the longitudinal axis, each of the proximal and distal ends having an opening therein,
an inner cannula configured to fit within the lumen of the outer cannula having a proximal end, a distal end, a longitudinal axis and a lumen extending from the proximal end to the oppositely disposed distal end along the longitudinal axis, the inner cannula including a slot defining an upper limit and a lower limit, the distal end having an expandable portion connected to the distal end that is configured to expand when the inner cannula is advanced out of the distal end of the outer cannula and to collapse when retracted back into the outer cannula,
wherein the expandable portion is constructed of polymer and shapeset material and configured to expand when the inner cannula is advanced out of the distal end of the outer cannula and to collapse when the retracted back into the outer cannula;
an actuator member including a in disposed with the inner cannula in contact with the elongated slot of the outer cannula wherein moving the actuator from a first position to a second position extends and retracts the expandable portion of the inner cannula from the distal end of the outer cannula; and
a locking mechanism configured to lock the inner cannula to the outer cannula.

11. An anchoring cannula of claim 10, wherein the distal end of the outer cannula has a cutting edge.

12. An anchoring cannula of claim 10 wherein the polymer is selected from the group consisting of polyaryletherketone (PAEK) including polyetheretherketone (PEEK), polyetherketoneketone (PEKK) and polyetherketone (PEK), carbon-PEEK composites, PEEK-BaSO.sub.4 polymeric rubbers, polyethylene terephthalate (PET), fabric, silicone, polyurethane, silicone-polyurethane copolymers based materials, polymeric rubbers, polyolefin rubbers, semi-rigid and rigid materials, thermoplastic elastomers, thermoset elastomers, elastomeric composites, rigid polymers including polyphenylene, polyamide, polyimide, polyetherimide, polyethylene, epoxy, and composites of metals and calcium-based ceramics, composites of PEEK and calcium based ceramics, and combinations thereof.

13. An anchoring cannula of claim 10 wherein the shapeset material is a Ni—Ti-based alloy such as Nitinol, an iron based alloy such as Fe—Mn—Si or Fe—Ni—Co-T, Cu—Al—Ni, Cu—Zn—Al and Fe—Mn—Si—Cr.

14. A method for treating a fracture comprising,
inserting the anchoring cannula of claim 1 into bone adjacent to a fracture;
advancing the second cannula out of the distal end of the first cannula wherein expanding the expandable portion so that the at least a part of the expandable portion is in contact with bone so as to stabilize the anchoring cannula in place;
treating the fracture adjacent to the anchoring cannula; and
retracting the second cannula back into the distal end of the outer cannula so as to collapse the expandable portion of the second cannula and removing the anchoring cannula from bone.

15. A method for treating a fracture in claim 14 further comprising the step of orientating the second cannula so that the lumen faces the fracture prior to advancing the second cannula so as to expand the expandable portion.

16. A method for treating a fracture in claim 15 wherein a material for treating the fracture is delivered through the lumen of the second cannula to the fracture.

17. A method for treating a fracture in claim 16 wherein the material for treating the fracture is selected from the group consisting of bone void filler, bone cement and bone graft materials.

18. A method for treating a fracture comprising:
inserting the anchoring cannula of claim 10 into bone adjacent to a fracture;
orientating the inner cannula so that the lumen of the inner cannula faces the fracture;
expanding the expandable portion of the inner cannula so that it is in contact with bone so as to stabilize the inner cannula in place;
delivering a material to treat the fracture through the lumen of the inner cannula to the fracture and adjacent area; and
collapsing the expandable portion of the second cannula and removing the anchoring cannula from the bone.

19. A method for treating a fracture of claim 14 wherein the fracture being treated is in a vertebrae, distal radius, proximal humerus and tibial plateau.

20. A method for treating a fracture of claim 18 wherein the fracture being treated is in a vertebrae, distal radius, proximal humerus and tibial plateau.

* * * * *

UNITED STATES PATENT AND TRADEMARK OFFICE
CERTIFICATE OF CORRECTION

| | | |
|---|---|---|
| PATENT NO. | : 8,852,253 B2 | Page 1 of 1 |
| APPLICATION NO. | : 13/360327 | |
| DATED | : October 7, 2014 | |
| INVENTOR(S) | : Mafi | |

It is certified that error appears in the above-identified patent and that said Letters Patent is hereby corrected as shown below:

In the Specification

In Column 3, Lines 44-45, delete "Calsium Sufacte" and insert -- Calcium Sulphate --, therefor.

In Column 4, Line 56, delete "cannula, 22," and insert -- cannula 22, --, therefor.

In Column 8, Line 3, delete "The se" and insert -- These --, therefor.

In the Claims

In Column 8, Line 49, in Claim 1, delete "a in" and insert -- a pin --, therefor.

In Column 9, Line 56, in Claim 10, delete "a in" and insert -- a pin --, therefor.

Signed and Sealed this
Twenty-eighth Day of April, 2015

Michelle K. Lee
*Director of the United States Patent and Trademark Office*